(12) United States Patent
Li et al.

(10) Patent No.: US 7,967,770 B2
(45) Date of Patent: Jun. 28, 2011

(54) IMPLANTABLE DRAINAGE DEVICE WITH PLANAR DUAL CURVED PORTION

(75) Inventors: Linsun Li, Nanjing (CN); Wenfeng Lu, Pfafftown, NC (US)

(73) Assignee: Cook Medical Technologies LLC IN (US)

( * ) Notice: Subject to any disclaimer, the term of this patent is extended or adjusted under 35 U.S.C. 154(b) by 447 days.

(21) Appl. No.: 12/019,456

(22) Filed: Jan. 24, 2008

(65) Prior Publication Data
US 2008/0249457 A1 Oct. 9, 2008

Related U.S. Application Data

(60) Provisional application No. 60/897,716, filed on Jan. 26, 2007.

(51) Int. Cl.
*A61M 37/00* (2006.01)
(52) U.S. Cl. .............................. 604/8; 604/19
(58) Field of Classification Search .................. 604/8, 7, 604/19, 164.05, 174–175, 264; 606/108
See application file for complete search history.

(56) References Cited

U.S. PATENT DOCUMENTS

| | | | | |
|---|---|---|---|---|
| 4,531,933 | A | 7/1985 | Norton et al. | 604/8 |
| 4,981,477 | A | 1/1991 | Schon et al. | 604/264 |
| 5,052,998 | A | 10/1991 | Zimmon | 604/8 |
| 5,129,910 | A | 7/1992 | Phan et al. | 606/127 |
| 5,259,847 | A * | 11/1993 | Trambert | 604/164.1 |
| 5,265,606 | A | 11/1993 | Kujawski | 128/632 |
| 5,466,242 | A | 11/1995 | Mori | 606/198 |
| 5,486,191 | A | 1/1996 | Pasricha et al. | 606/191 |

(Continued)

FOREIGN PATENT DOCUMENTS

| | | |
|---|---|---|
| CA | 1232705 | 2/1988 |
| WO | WO 2006/074283 A2 | 7/2006 |

OTHER PUBLICATIONS

International Search Report and Written Opinion dated May 23, 2008, from International Application No. PCT/US2008/051927.

*Primary Examiner* — Tatyana Zalukaeva
*Assistant Examiner* — Benedict L Hanrahan
(74) *Attorney, Agent, or Firm* — Brinks Hofer Gilson & Lione

(57) ABSTRACT

In a first embodiment, implantable drainage devices with a curvilinear portion are provided, such as stents or drainage catheters formed as a tubular member having a curvilinear portion comprising one or more pairs of adjacent bends curved in opposite directions. The drainage devices house a drainage lumen that may extend through the curvilinear portion, which may be dimensioned to retain the drainage device within a body vessel and provide a desired fluid conductance through a tortuous portion of the drainage lumen within the curvilinear portion. The curvilinear portion may include two or more planar bends facing in opposite directions. The drainage device is preferably a biliary stent or drainage catheter constructed of thermoplastic material resilient enough to permit the bends of the curvilinear portion to straighten in response to placement of a guidewire through the drainage lumen, and to permit a portion of the tubular member to again form the plurality of bends when the guidewire is removed from the drainage lumen. In a second embodiment, methods of implanting the drainage devices within a body vessel, such as a biliary duct, are provided. For example, the drainage device may be a biliary stent implanted within the Papilla of Vater (e.g, within a biliary or pancreatic duct) without traversing the Sphincter of Oddi.

17 Claims, 7 Drawing Sheets

U.S. PATENT DOCUMENTS

| | | | |
|---|---|---|---|
| 5,902,284 A | 5/1999 | Suzuki et al. | 604/265 |
| 6,902,555 B2 | 6/2005 | Paskar | 604/500 |
| 7,041,139 B2 | 5/2006 | Bluni et al. | 623/23.66 |
| 7,682,401 B2 * | 3/2010 | Deal | 623/23.66 |
| 2003/0074082 A1 | 4/2003 | Bottcher et al. | 623/23.7 |
| 2004/0249436 A1 | 12/2004 | Azoian et al. | 623/1.15 |
| 2005/0070821 A1 | 3/2005 | Deal et al. | 600/585 |
| 2005/0125050 A1 | 6/2005 | Carter et al. | 623/1.11 |
| 2006/0052879 A1 | 3/2006 | Kolb | 623/23.7 |
| 2006/0167538 A1 | 7/2006 | Rucker | 623/1.25 |

* cited by examiner

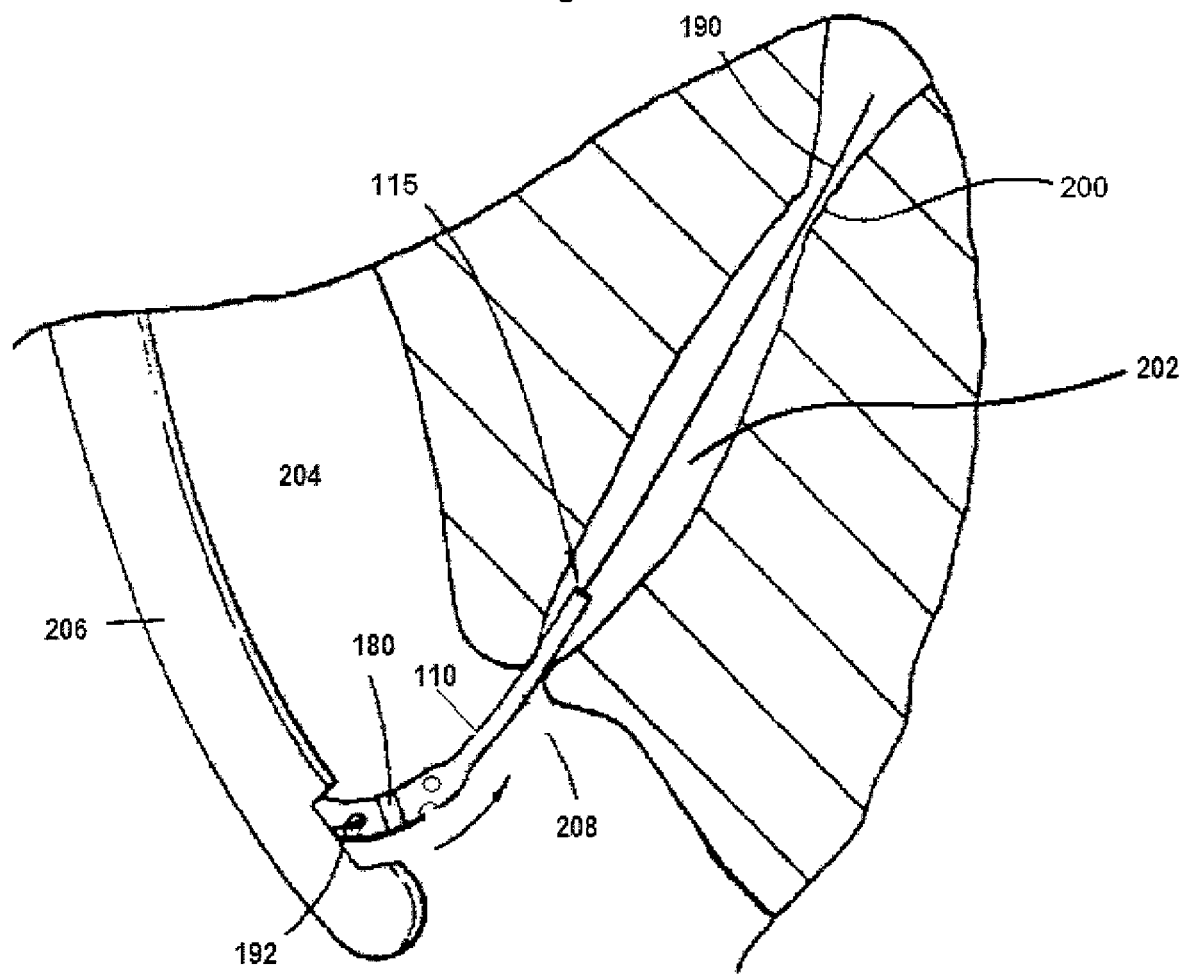

IMPLANTABLE DRAINAGE DEVICE WITH PLANAR DUAL CURVED PORTION

RELATED APPLICATIONS

This application claims the benefit of U.S. Provisional Patent Application Ser. No. 60/897,716, filed Jan. 26, 2007, which is incorporated herein by reference in its entirety.

TECHNICAL FIELD

The present invention relates to implantable medical devices. More particularly, the invention relates to implantable drainage devices, including drainage stents or indwelling catheters, adapted for use in the biliary tract and to methods for implanting the devices.

BACKGROUND

Drainage devices may be implanted to treat various conditions. For example, drainage stents configured as biliary stents may be implanted in the biliary tract to treat obstructive jaundice. FIG. 1 is illustrative of a typical biliary system showing: a right hepatic duct 1a joining with the left hepatic duct 1b to form a common hepatic duct 6; a gall bladder 5 and a cystic duct 3; a pancreas 7 and a pancreatic duct 9; and all aforementioned ducts connecting to form a common bile duct 2 leading to a duodenum 4 through the Papilla of Vater 8 and Sphincter of Oddi. Biliary stenting treatment approaches can be used to provide short-term treatment of conditions such as biliary fistulae or giant common duct stones. Biliary stents may be implanted to treat chronic conditions such as postoperative biliary stricture, primary sclerosing cholangitis and chronic pancreatitis. An implanted biliary stent may permit digestive liquids to flow through the biliary stent lumen into the duodenum and the digestive tract.

A drainage device, such as a drainage stent or catheter, can be configured as a tubular member defining a drainage lumen that can be advanced on a delivery system into a body vessel, such as the bile duct, where the drainage device is deployed. Typically, the tubular member includes one or more perforations communicating between an exterior surface of the tubular member and the drainage lumen. The tubular member preferably has sufficient radial strength to resist collapse and to maintain an open body vessel lumen upon implantation. The tubular member is preferably longitudinally flexible enough to be advanced during delivery along a guidewire through a path that may include sharp bends.

To secure the drainage stent at a site of implantation within the body vessel, the tubular member may include a means for retaining the drainage stent within a body vessel, such as retention flaps radially projecting from the tubular body. Retention flaps may be formed by making an oblique slit along the length of the tubular member. Each slit defines a tab and enables the tab to project slightly radially outwardly of the outer surface of the tube to engage the luminal surface of the biliary duct to prevent migration. The tabs at the opposite ends of the drainage stent typically extend toward the middle of the stent as well as radially outward. The openings defined by the tab-forming skives may provide access to the interior of the stent of cellular or other material that may tend to develop into an obstruction tending to restrict flow through the stent. Alternatively, drainage stents may include one or more curled or coiled end portions. For example, the distal and/or proximal ends of a drainage stent may have a curled configuration, often referred to as a "pigtail" configuration. One such example is shown by U.S. Pat. No. 5,052,998 to Zimmon which discloses an indwelling drainage stent having flaps at one end, a series of drainage perforations along the length of the drainage stent and a pigtail configuration at the opposite end. Other stents include anchoring flaps or pigtail loops at both ends of the stent. Prior art stents have been provided both with and without the drainage perforations as shown in the Zimmon patent. Other structures, such as helical tubular drainage stents having an inflatable portion, are disclosed by Rucker in US 2006/0167538A1, filed Dec. 21, 2005. Kolb describes drainage stents having one or more curled portions and a drainage channel having a laterally open portion in US 2006/0052879 A1, filed Aug. 16, 2005.

Tubular biliary stents are typically implanted with a delivery system having the stent mounted on the distal end of a guidewire. After the stent has been advanced along a guidewire and manipulated into the intended deployment site in the biliary duct, the stent is released and the delivery device is retracted, thereby leaving the stent within the biliary tract. For example, biliary drainage stents are typically advanced on a delivery catheter through an endoscope and deployed in a bile duct. Biliary and pancreatic stents are typically pushed into place by a "pusher" catheter which is advanced from behind the stent and pushes against the proximal end of the stent until the stent has reached its desired location. The distal end of the delivery catheter generally must pass through the Papilla of Vater, for example by passing a drainage stent through the Sphincter of Oddi. An uncompromised Sphincter of Oddi acts a one-valve letting biliary drainage to flow only toward the duodenum.

However, during the placement procedure, conventional structures for retaining the drainage stent within the body passage, such as flaps or curled ends, may irritate ductal tissue as they pass through the duct, which may lead to inflammation of the duct. Conventional drainage stent structures for retaining the drainage stent in position after implantation may also cause aggravation to the ductal tissue while the stent is left in place, or when the drainage stent is removed. Furthermore, insertion of a drainage stent placed by endoscopic sphincterotomy may require stretching and cutting of the Sphincter of Oddi and surrounding areas, which may compromise the function of the Sphincter of Oddi after insertion of the drainage stent. In addition to the sphincterotomy procedure for inserting a drainage stent, placement of the position of the biliary stent at the Papilla of Vater (e.g., across the Sphincter of Oddi) may also lead to duodenobiliary reflux. A compromised Sphincter of Oddi may allow fluid flow in the reverse direction from the duodenum, or duodenobiliary reflux, causing bacteria and biofilm deposition, and possibly occluding the biliary duct or the drainage stent.

Therefore, there exists a need for an improved drainage device which can be retained within a body vessel, such as a biliary or pancreatic duct, with reduced irritation to the body tissue, and which may be removed without damaging the body vessel. Furthermore, there exists a need for an improved method or procedure of implanting the drainage device without compromising the Sphincter of Oddi, and reducing the risk of duodenobiliary reflux.

SUMMARY

In a first embodiment, drainage structures are provided. The drainage structures preferably include a tubular member having a curvilinear portion defining a drainage lumen comprising one or more pairs of adjacent bends curved in opposite directions. The drainage device may include a tubular member having proximal and distal ends, interior and exterior surfaces, and an inner lumen disposed within the interior surface between the proximal end and the distal end. The tubular member can define a drainage lumen that extends from an inlet to an outlet. The tubular member may also include a substantially linear portion and a curvilinear portion. The curvilinear portion may have a plurality of planar curvilinear bends formed by adjacent curvilinear bends curved in opposite directions with respect to one another. Perforations may optionally be included along portions of the tubular member to facilitate drainage along the length of the drainage stent. For example, the tubular member may have an "S-shaped" curvilinear portion having one or more perforations (e.g., drainage holes) between the drainage lumen and the external surface of the curvilinear portion. One or more portions of the tubular member may include a substantially planar configuration, such as a dual-curved (i.e., "S-"shaped) portion formed by a pair of two consecutive curvilinear bends curved in opposite directions with respect to one another. The interior surface of the curvilinear bent portion of the tubular member preferably defines a tortuous portion of the drainage lumen. The exterior surface of the curvilinear portion of the drainage device preferably has a width measured perpendicular to the longitudinal axis of the device that is approximately equal to the diameter of a body vessel at a site of implantation. For example, the width of an "S-shaped" curvilinear portion is approximately equal to or greater than the diameter of the common bile duct (e.g., about 10 mm). The curvilinear bends are preferably included in the distal portion of a drainage stent that includes the inlet, although drainage devices may also include curvilinear portions in other portions, or more than one portion, of the device. The tubular member may be made of a suitably flexible biocompatible material which is resiliently compliant so as to allow the drainage stent to readily conform to the curvature of a ductal passageway within a body vessel. The curvilinear portion being resiliently formable between a bent configuration and a linear configuration. The bent configuration includes a pair of adjacent curvilinear bends in the tubular member bent in opposite directions with respect to one another and radially bisected by a hypothetical plane containing the longitudinal axis; the linear configuration may be formed by extending the drainage device along the longitudinal axis until the longitudinal axis is contained within the drainage lumen between the proximal end and the distal end.

In a second embodiment, methods of implanting a drainage device are provided comprising the steps of implanting one or more drainage devices of the first embodiment. A method of deploying a drainage device comprising the steps of inserting the drainage device into a body vessel in a linear configuration, delivering the drainage device in the linear configuration to a point of treatment; and deploying the drainage device at the point of treatment in the bent configuration with the pair of curvilinear bends securing the drainage device within the body vessel and permitting fluid to flow through the drainage lumen. The point of treatment may be a biliary or pancreatic duct. Preferably, the drainage structure is implanted within the Papilla of Vater (e.g, within a biliary or pancreatic duct) without transversing the Sphincter of Oddi. For example, one method of positioning an indwelling stent in a patient may include the step of inserting a guidewire to a point of treatment within a body vessel in a patient. Another step may include placing a drainage lumen of a drainage device around the guidewire. Advancing the drainage device along the guidewire through the body vessel to the point of treatment may also be provided. Another step may be withdrawing the guidewire. Most preferably, methods of implanting a drainage device include percutaneously inserting the device along a guidewire through a hepatic duct. Alternatively, the drainage device may be inserted from within the duodenum through an endoscope (e.g., ERCP). Preferably, the drainage device is implanted within a body vessel that is a biliary duct. Methods of implanting a drainage device may include imaging a point of treatment within the biliary duct to determine a position of a drainage device. The drainage device may be inserted by percutaneous transhepatic cholangiogram (PTC) by inserting a needle through a liver of the patient may also be provided. This embodiment may also include the step of inserting a guidewire through the liver and through one of the right and left hepatic ducts of the patient to the point of treatment. Another step may include placing a drainage lumen of a drainage device around the guidewire. Advancing the drainage device along the guidewire to the point of treatment, with a portion being advanced through a portion of a common bile duct of a patient where the linear portion is proximate the point of treatment, the portion of the common bile duct being near a Sphincter of Oddi and a Papilla of Vater of the patient. Another step may include withdrawing the guidewire, with a portion of the drainage device contacting a wall of the common bile duct.

BRIEF DESCRIPTION OF THE DRAWINGS

FIG. 5A shows the delivery of the drainage device into a biliary duct

DETAILED DESCRIPTION

Figure 1:
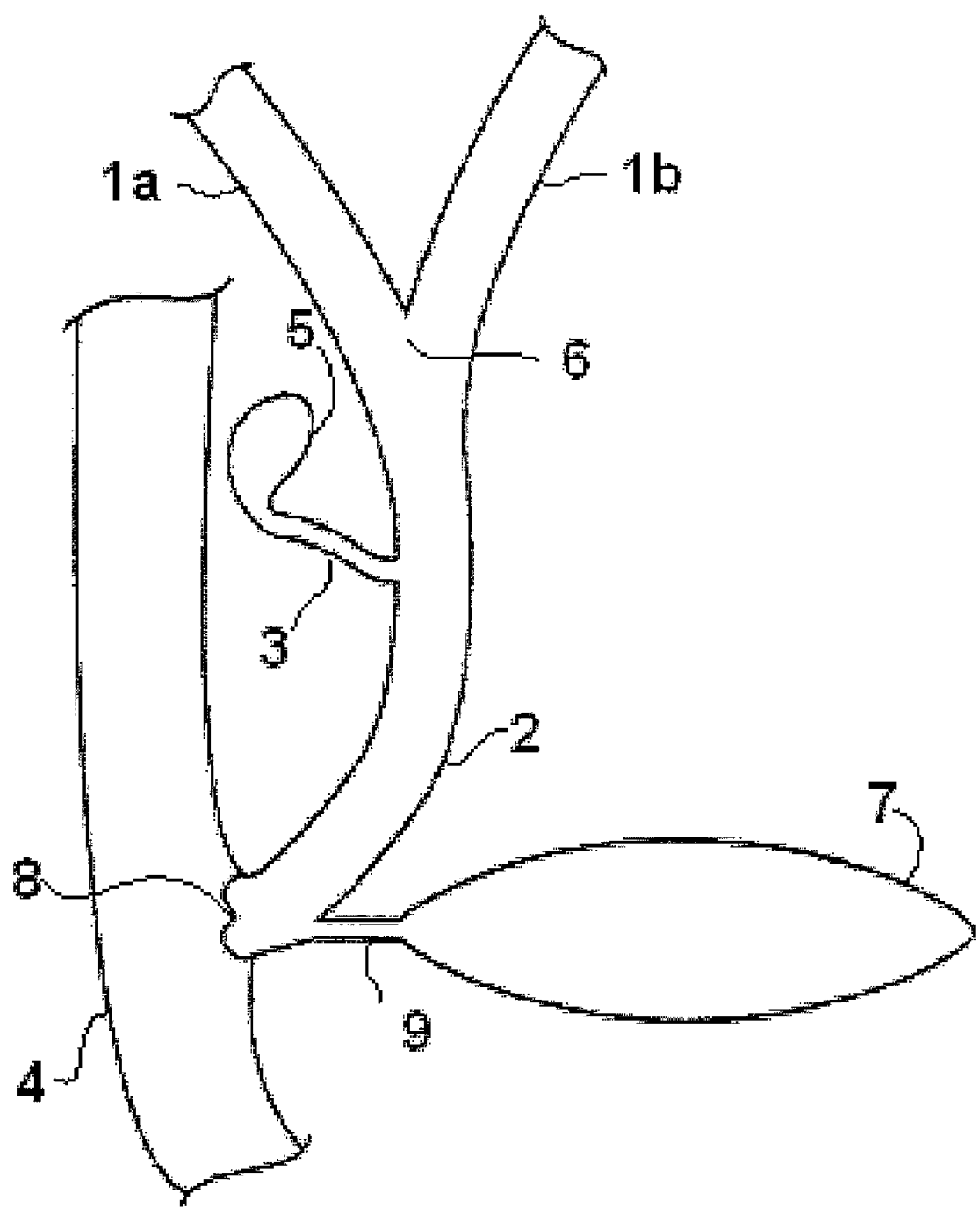
FIG. 1 shows a typical binary system.

The following detailed description and appended drawings describe and illustrate various exemplary embodiments of the invention. The description and drawings serve to enable one skilled in the art to make and use the invention. Although the present invention will be described with reference to preferred embodiments, those skilled in the art will recognize that changes may be made in form and detail without departing from the spirit and scope of the invention. As such, it is intended that the following detailed description be regarded as illustrative rather than limiting and that it is the appended claims, including all equivalents thereof, which are intended to define the scope of the invention In the present application, the term "proximal" refers to a direction that is generally towards a physician during a medical procedure, while the term "distal" refers to a direction that is generally towards a target site within a patient's anatomy during a medical procedure.

As used herein the terms "comprise(s)," "include(s)," "having," "has," "contain(s)," and variants thereof, are intended to be open-ended transitional phrases, terms, or words that do not preclude the possibility of additional acts or structure.

As used herein, the term "body vessel" means any body passage cavity that conducts fluid, including but not limited to biliary ducts, pancreatic ducts, ureteral passages, esophagus, and blood vessels such as those of the human vasculature system.

As used herein, the term "implantable" refers to an ability of a medical device to be positioned at a location within a body, such as within a body vessel. Furthermore, the terms "implantation" and "implanted" refer to the positioning of a medical device at a location within a body, such as within a body vessel.

As used herein, "endolumenally," "intraluminal" or "transluminal" all refer synonymously to implantation placement by procedures wherein the medical device is advanced within and through the lumen of a body vessel from a remote location to a target site within the body vessel. Endolumenal delivery includes implantation in a biliary duct from an endoscope or catheter.

Various medical devices for implantation in a body vessel are disclosed herein. Preferred embodiments relate to a medical drainage device comprising a two or more planar curvilinear bends in a tubular member, where each bend is curved in opposite directions with respect to adjacent bends. For instance, a pair of consecutive planar curvilinear bends may form an "S"-shaped or sinusoidal configuration. Also preferably, the curvilinear bends define a tortuous portion of the drainage lumen within the tubular member. The medical drainage devices are described with respect to an exemplary biliary stent embodiment comprising a tubular support member. However, the embodiments of biliary drainage stent also illustrate other drainage devices, such as ureteral stents, esophageal stents or drainage catheters provided in accordance with other embodiments. For example, a drainage stent could be configured for use within a ureteral, urethral, esophageal or blood vessel.

Figure 2A:
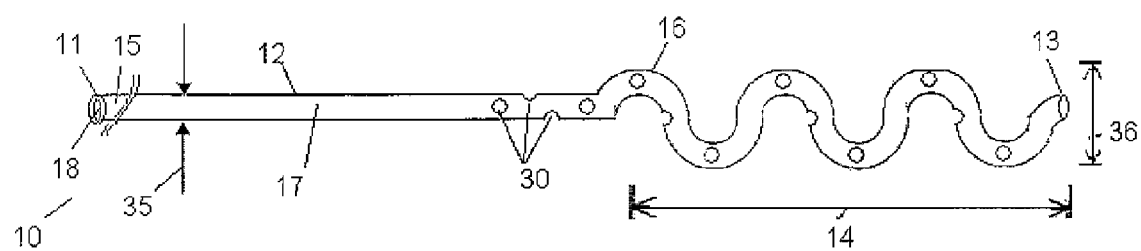
FIG. 2A is a side view of a drainage device
Figure 2B:
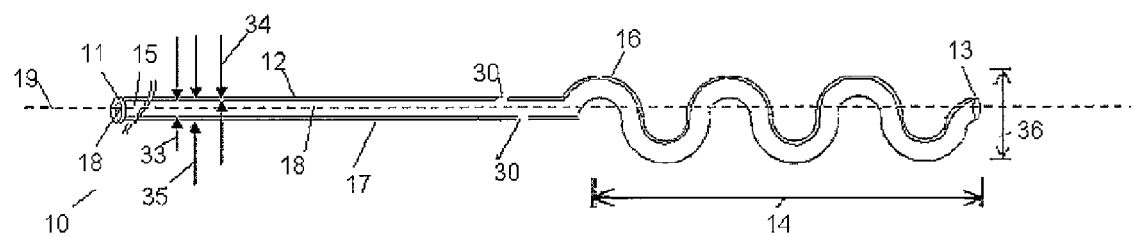
FIG. 2B is a longitudinal cross sectional view of a portion of the drainage device shown in FIG. 2A.

In a first embodiment, implantable drainage devices are provided. The devices are preferably configured as indwelling implantable medical drainage device adapted for placement within a body vessel and including a means for retaining the drainage device within the body vessel. FIG. 2A shows one example of a drainage device configured as a stent 10 or the distal end of an indwelling drainage catheter comprising a means for retaining the drainage stent 10 within a body vessel. Referring to FIG. 2A, a drainage device configured as a drainage stent 10 has a tubular member 12 extending from an inlet 11 to an outlet 13. The tubular member 12 may include a proximal portion 15 extending from the inlet 11, a distal portion 14 extending from the outlet 13 and a central portion 17 disposed therebetween. The tubular member 12 has an exterior surface, an interior surface defining a drainage lumen 18 and a plurality of drainage holes 30. FIG. 2B is a cross-sectional view of the drainage stent 10 shown in FIG. 2A. The proximal portion 15 and the central portion 17 of the tubular member 12 is radially aligned along a longitudinal axis 19 within the drainage lumen 18, and at the outlet 13. The plurality of curvilinear bends 16 in the rest of the distal portion 14 may be symmetrically disposed on alternating sides of the longitudinal axis 19. The tubular member 12 may have an external diameter 34, a thickness 34, and define a drainage lumen 18 having a diameter 33. The thickness 34 of the tubular member is preferably substantially uniform along the length of the drainage stent 10. Alternatively, the thickness of the tubular member 12 may vary along the length and/or circumference of the tubular member 12. For example, the tubular member 12 may have ridges along the outer wall for facilitating fluid flow around the external surface. The tubular member 12 may include one or more structures to facilitate or direct fluid flow around the tubular member 12 within a body vessel. For example, U.S. Pat. No. 5,129,910 to Phan et al. discloses a stent having a helical-like ridge along at least a portion of the outer wall for expelling masses within a body passage. The helical-like ridge may include a smooth, convex superior surface having a beveled central portion and a concave inferior surface.

A plurality of drainage holes 30 may extend through the thickness 34 of the drainage stent 10, between the drainage lumen 18 and the external surface of the tubular member 12. The tubular member 12 can be configured as a continuous uninterrupted tube adapted to provide a drainage lumen 18 through an obstructed portion of a body vessel, such as a biliary duct. The tubular member 12 is preferably longitudinally flexible enough to be advanced during delivery along a guidewire through a path that may include sharp bends. Instead of forming a drainage stent 10, the tubular member 12 may be a catheter. The distal portion 14 of the catheter may be thermoformed into a series of curvilinear bends 16 to secure the catheter within a body vessel, for example to provide an indwelling drainage conduit. Optionally, the internal and/or external surface of the tubular member may be roughened, for example to prevent deposition of bacteria. For example, U.S. Pat. No. 5,902,284 to Yasuyuki et al. describe a means for setting surface roughness of the inner surface of an indwelling medical tube to about 0.5 micrometer or less to prevent deposition of bacteria on the surface.

The drainage stent 10 may be configured for placement within a biliary or pancreatic duct with the tubular member 12 extending the length of the duct and with the outlet 13 positioned proximate the Sphincter of Oddi. Preferably, the drainage stent 10 is configured for retention within the duct without extending across the Sphincter of Oddi or into the duodenum. The tubular member 12 comprises a proximal portion 15 extending from the inlet 11 along a substantially straight central portion 17. Alternatively, proximal portion 15 may be configured as an extended drainage catheter having a desired length. For example, a portion of the proximal portion 15 may be positioned outside the body, for example as the proximal end of a drainage catheter. Typically, the central portion 17 is formed as a tubular member defining a drainage lumen 18 extending from the inlet 11 to the outlet 13. Optionally, medical drainage device may be a drainage catheter and the central portion 17 may house multiple lumens and may include one or more inflatable balloons along the exterior surface of the tubular member 12. The distal portion 14 is preferably configured to secure the drainage stent 10 or other medical drainage device within a body vessel upon deployment at a point of treatment.

Preferably, at least a portion of the tubular member 12 forms a means for retaining the drainage device 10 in a body vessel. For example, the drainage stent 10 is securable within the body vessel by a flexible resilient distal portion 14 comprising two or more planar curvilinear bends 16. The curvilinear bends 16 of the distal portion 14 preferably include one or more "S-"shaped portions formed by this series of consecutive curvilinear bends in the tubular member 12 oriented in consecutively opposite directions with respect to one another. Preferably, at least one of the "S-"shaped portions in the curvilinear bends 16 is symmetrical about a transverse plane including the longitudinal axis 19 bisecting the drainage stent 10, so as to form a pair of planar curves. The number, size and orientation of the curvilinear bends 16 can be modified to accommodate the migration-preventing requirements of the particular medical drainage device to be implanted, the site of implantation and the desired function of the device. For example, the maximum width 36 of the curvilinear bends 16 in the distal portion 14 of the tubular member 12 is preferably about the width of the body vessel at the intended point of implantation. For example, the width 36 may be about 10 mm or less to retain a drainage stent 10 within the biliary duct. In some embodiments, the proximal portion 15 and/or the central portion 17 of the tubular member 12 may include one or more curvilinear bends 16. The distal portion 14 may have any therapeutically effective length measured along the longitudinal axis 19. Most preferably, the distal portion 14 of the tubular member 12 comprises a plurality of substantially similar planar curvilinear bends 16, with adjacent bends oriented in opposite directions. When the drainage stent 10 is configured as a biliary stent, a distal portion 14 including any suitable number of curvilinear bends 16 is preferably oriented closer to the Sphincter of Oddi within the biliary or pancreatic duct than the proximal portion 15. However, any portion 15, 17, 14 of the tubular member 12 may include a plurality of planar curvilinear bends 16.

The curvilinear bends 16 are preferably configured to provide a means for retaining the tubular member 12 within a body vessel, while permitting sufficient conduction of fluid through the fluid drainage lumen 18 passing through the distal portion 14. Therefore, the curvilinear bends 16 may be pronounced enough (e.g., having a sufficient width 36) to anchor the tubular member 12 within the body vessel, while also housing a fluid drainage lumen 18 with a geometry having a resistance to fluid flow and total length suitable to provide adequate fluid drainage. For example, if the drainage lumen 18 passing through curvilinear bends 16 of a biliary stent is too long of includes regions where biofluid can stagnate, the drainage lumen may become clogged or restricted by biofilm deposition. Therefore, the curvilinear bends 16 are preferably oriented in a "planar" configuration, meaning that the drainage lumen 18 enclosed within the curvilinear bends 16 follows a tortuous path having a series of bends in substantially two dimensions. The curvilinear bends 16 may be bisected by a plane including the longitudinal axis 19. Preferably, the curvilinear bends 16 do not form a helical or spiral structure. Helical or spiral bend structures may provide a longer and more tortuous drainage lumen 18 path than that of the curvilinear bends 16. FIG. 3 shows a detailed longitudinal cross-sectional view of the distal portion 14 of the implantable drainage stent 10 shown in FIGS. 2A and 2B. A portion of the drainage lumen 18 is shown extending from the distal end of the central portion 17 of the tubular member 12, through a tortuous lumen passing through five consecutive bends 23 forming the plurality of curvilinear bends 16. The longitudinal axis 19 of the tubular member 12 is shown centered within the drainage lumen 18 in the central portion 17. The bends 23 have a radius 25, defined as the radius of curvature measured from the longitudinal axis 19 to the interior of the bend 23. The bends 23 are shown with substantially equal radii 25, although other embodiments provide bends 23 with radii 25$a$, 25$b$, 25$c$ and 25$d$ that may be the same or different from one another. Preferably, the radii 25 of adjacent bends 23 of the tubular member 12 are substantially equal. For example, the first radius 25$a$ is substantially equal to the second radius 25$b$, the second radius 25$b$ may be substantially equal to the third radius 25$c$, and the third radius 25$c$ may be substantially equal to the fourth radius 25$d$.

Figure 3A:
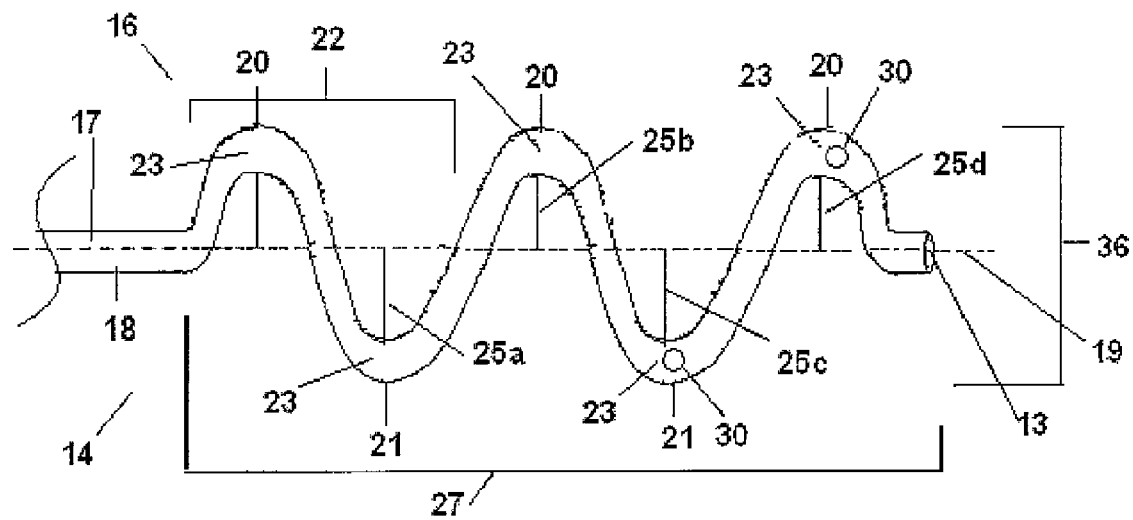
FIG. 3A is a detail cross sectional view of a bent portion of the drainage device shown in FIG. 2B.

While each of the curvilinear bends 16 shown in FIG. 3A subtends an angle of about 180°, the distal portion 14 preferably includes a pair of adjacent bends 16 oriented in opposite directions that are substantially co-planar and subtend an angle of less than 360°, preferably less than 270° and most preferably about 180°. A longitudinal cross sectional plane containing the longitudinal axis 19 bisects the bends 23 shown in FIG. 3. The portion comprising the plurality of planar curvilinear bends 16 may be formed in a variety of configurations of bends 23, varying number and size of bends 23, and different depths and pitches to accommodate different delivery devices and different anatomical features of the body vessel at the site of implantation. The plurality of planar curvilinear bends 16 preferably forms a sinusoidal pattern where all of the bends 23 are bisected by a hypothetical symmetry plane containing the longitudinal axis 19, where the bends 23 do not form a helical configuration.

The dimensions of the planar curvilinear bends 16 may vary depending on the intended application and location of the curvilinear bends 16 in the medical drainage device. For a biliary drainage stent 10 shown in FIGS. 2A and 2B, the planar curvilinear bends 16 form a series of consecutive "S-"shaped bends. FIG. 3 shows a detailed view of a plurality of planar curvilinear bends 16 in the distal portion 14 portion of a drainage stent 10 including a total of five bends 23. The total longitudinal length 27 of the plurality of planar curvilinear bends 16 is preferably about 5-50 mm, more preferably about 10-35 mm, and most preferably about 20, 21, 22, 23, 24 or 25 mm. The longitudinal length 22, or wavelength, of each pair of adjacent bends 23 is preferably about 1-20 mm, preferably about 1-10 mm and most preferably about 5, 6, 7 or 8 mm. The lateral distance 36, or peak-to-peak amplitude, between inflection points 20, 21 of adjacent bends 23 in the plurality of planar curvilinear bends 16 is typically about 1-20 mm, preferably about 8-12 mm, and most preferably about 8, 9, 10, 11 or 12 mm. The lateral distance 36 may be measured perpendicular to the longitudinal axis 19, and may be sized to be greater than or equal to the cross sectional distance of the biliary duct or common bile duct, if applicable. Preferably, the inflection points 20 on a first side of the plurality of planar curvilinear bends 16 are positioned at about the same distance from the longitudinal axis 19 as the inflection points 21 on the opposite lateral side of the plurality of planar curvilinear bends 16. In other words, the bends 23 are preferably symmetrically arrayed with respect to the longitudinal axis 19, extending a lateral distance of about 4, 5 or 6 mm on either side of the longitudinal axis (i.e., the distance, or amplitude, between the inflection points 20 and the longitudinal axis 19 and the distance between the inflection points 21 and the longitudinal axis 19 may both be about equal to about half the lateral distance 36).

Figure 3B:
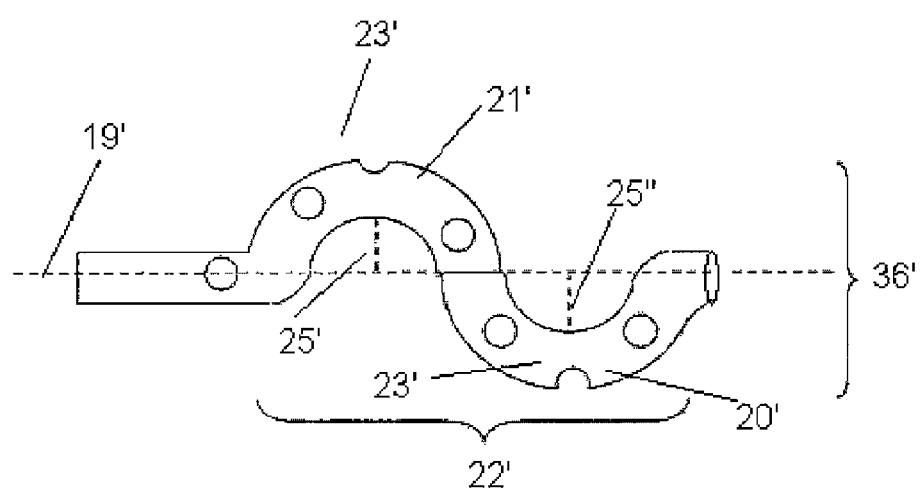
FIG. 3B is a detail cross sectional view of a bent portion of the drainage device.

Preferably, the ratio between the longitudinal length 22 and the lateral width 36 of each pair of consecutive bends 23 forming an "S-"shaped configuration in the plurality of curvilinear bends 16 is between about 1.0:1.0 and about 1.0:20.0, and more preferably about 10:1.6 and 1.0:2.4. FIG. 3B shows one pair of consecutive bends 23' having a longitudinal length 22' and a lateral distance 36' about the longitudinal axis 19' sized to be equal to the cross sectional distance of the common bile duct. Table 1 below provides ratios of particularly preferred dimensions for the longitudinal length 22' of a single "S-"shaped pair of bends in the plurality of curvilinear bends 16' and the lateral distance 36' between inflection points 20', 21 of adjacent bends in the same single "S-"shaped bend. The internal radius 25 of each curvilinear bend 16' and the ratio of the length to the width of each curvilinear bend 16' is preferably selected to balance the concerns of providing adequate retention of the tubular member 12 within the body vessel and providing adequate fluid conductance through the drainage lumen 18. The length of each curvilinear bend 16' is measured along the longitudinal axis 19 bisecting the outlet 13 of the drainage stent 10 (and preferably also bisecting an unbent central portion 17 of the tubular member 12); the width of each curvilinear bend 16' is measured perpendicular to the longitudinal axis 19. In some examples, the internal radius 25 (r) for a pair of two congruent adjacent curvilinear bends 16' shown in FIG. 3B may be estimated by the relationship: $r=(w/2)-d$, where w is the width (36') of the pair of adjacent curvilinear bends and d is the external diameter of the tubular member. The ratio of the length to the width (lateral distance) for each curvilinear bend 16 is preferably selected to provide a desired rate of fluid flow through the drainage lumen 18, while providing sufficiently atraumatic resistance to movement of the tubular member 12 within a body vessel. Examples of preferred ratios are shown in Table 1 below, with ratios between about 0.42 and 1.00 being particularly preferred for biliary drainage applications (i.e., the longitudinal length 22 is about 42%-100% of the lateral distance 36), including without limitation the following ratios: 0.42, 0.45, 0.50, 0.55, 0.56, 0.58, 0.6, 0.63, 0.64, 0.67, 0.67, 0.70, 0.71, 0.73, 0.75, 0.78, 0.8, 0.83, 0.85, 0.88, 0.89, 1.00, 1.14, 1.17, 1.20, 1.33, 1.40, 1.60 and intervals of 0.01 therebetween. Each of the consecutive bends 23' have a substantially equal internal radius 25', 25" measured between the longitudinal axis 19' and the outer surface of the tubular member 12 at each inflection point 20', 21'.

TABLE 1

Ratios for Preferred Adjacent Bends

| Lateral distance (mm) | Longitudinal Length (mm) | | | |
|---|---|---|---|---|
|  | 5 | 6 | 7 | 8 |
| 5 | 1.00 | 1.20 | 1.40 | 1.60 |
| 6 | 0.83 | 1.00 | 1.17 | 1.33 |
| 7 | 0.71 | 0.85 | 1.00 | 1.14 |
| 8 | 0.63 | 0.75 | 0.88 | 1.00 |
| 9 | 0.56 | 0.67 | 0.78 | 0.89 |
| 10 | 0.50 | 0.60 | 0.70 | 0.80 |
| 11 | 0.45 | 0.55 | 0.64 | 0.73 |
| 12 | 0.42 | 0.50 | 0.58 | 0.67 |

Referring to FIG. 2A, the tubular member 12 may have any suitable length and external diameter depending on the intended use of the medical drainage device. Preferably, the external diameter 35 is sized to fit securably within an occluded biliary duct. For example, a biliary stent may have an external diameter 35 of about 5-12 French (1.6-4.0 mm) and a length of about 3-20 cm, preferably about 8-15 cm, between the inlet 11 and the outlet 13. In one embodiment including a biliary or pancreatic drainage catheter, the drainage device may have an external diameter 35 of about 5-15 French (1.6-5.0 mm), a length of about 30-50 cm, preferably about 35-45 cm, between the inlet 11 and the outlet 13, and a tube wall thickness 34 of at least 0.35 mm. For another embodiment including a nasobiliary drainage catheter, the drainage device may have an external diameter 35 of about 5-15 French (1.6-5.0 mm) and a length of about 150-300 cm, preferably about 200-250 cm, between the inlet 11 and the outlet 13. One preferred drainage stent 10 comprises a tubular member 12 having an external diameter 35 of about 8.5 French, although external diameters 35 of 5, 6, 7, 8, 9, 10, 11 or 12 French, or 0.5 French measurements therebetween, are also suitable. For catheters forming drainage tubes, the tubular member 12 may be considerably longer, so as to extend from inside a patient to a drainage collection receptacle. As shown in FIG. 2B, showing a longitudinal cross section of the drainage stent 10 shown in FIG. 2A, the inner diameter 33 of the drainage lumen 18 is preferably large enough to maintain a desired rate of fluid drainage therethrough while preventing clogging due to biofilm deposition. For example, an inner diameter 33 of about 1.5 mm to about 3.5 mm can be used.

FIG. 2B is a longitudinal cross sectional view of a portion of the drainage device shown in FIG. 2A. The tubular member 12 defines a drainage lumen 18 extending from the inlet 11 to the outlet 13. A longitudinal axis 19 of the tubular member 12 is positioned in the central portion 17. In the distal portion 14, the drainage lumen 18 has a tortuous configuration passing through a series of the planar curvilinear bends 16 between the central portion 17 and the inlet 11. Preferably, the inlet 11 is configured to permit fluid to enter the drainage lumen 18, which is configured to conduct fluid from the proximal portion 15, through the central portion 17 and the distal portion 14 to the outlet 13. Optionally, the inlet 11 can be configured to permit fluid to enter the drainage lumen 18, which is configured to conduct fluid from the distal portion 14, through the central portion 17 to the inlet 11.

The tubular member 12 may optionally comprise a plurality of drainage holes 30. The number, position and size of the drainage holes 30 may be selected to provide a desired rate of fluid flow into, through, and/or out of the drainage stent 10. Typically, the central portion 17 or distal portion 14 comprises enough drainage holes 30 of a desired caliber to provide a desired rate of fluid flow into the drainage stent 10. The holes 30 should be large enough to permit collection of fluid in the drainage stent 10 at a desired rate without occlusion due to biodeposition within a body vessel, but small enough to permit a desired rate of fluid flow through the entire length of the drainage stent 10. Typically, holes 30 may have a diameter of about 0.1 to 1.0 mm. Preferably, the drainage stent 10 is configured and placed to provide fluid flow from the proximal portion 15 to the distal portion 14 of the tubular member 12. Alternatively, a drainage stent 10 may be placed and configured for fluid flow in the opposite direction, from the distal portion 14 to the proximal portion 15.

The tubular member 12 can be formed from any suitable material providing sufficient radial strength to resist collapse and to maintain an open body vessel lumen upon implantation. Typically, tubular members 12 are formed from a biocompatible polymer. The tubular member 12 is preferably resiliently deformable to conform readily to the curvature of the biliary duct, while having sufficient "hoop" strength to retain form and patency within the biliary duct. Preferably, the tubular member 12 is formed from a thermoformable material that can be extruded or molded. The tubular member 12 may be formed from a polyolefin such as a metallocene catalyzed polyethylene, polypropylene, polybutylene or copolymers thereof. Preferably, the tubular member 12 is formed from a biocompatible polyethylene. Other suitable materials for the tubular member 12 include polyurethane (such as a material commercially available from Dow Corning under the trade name PELLETHANE), a silicone rubber (such as a material commercially available from Dow Corning under the trade name SILASTIC) and a polyetheretherketone (such as a material commercially available from Victrex under the trade name PEEK). Suitable tubular member 12 materials also include: vinyl aromatic polymers such as polystyrene; vinyl aromatic copolymers such as styrene-isobutylene copolymers and butadiene-styrene copolymers; ethylenic copolymers such as ethylene vinyl acetate (EVA), ethylene-methacrylic acid and ethylene-acrylic acid copolymers where some of the acid groups have been neutralized with either zinc or sodium ions (commonly known as ionomers); polyacetals; chloropolymers such as polyvinylchloride (PVC); polyesters such as polyethyleneterephthalate (PET); polyester-ethers; polyamides such as nylon 6 and nylon 6,6; polyamide ethers; polyethers; elastomers such as elastomeric polyurethanes and polyurethane copolymers; silicones; and polycarbonates, as well as mixtures and block or random copolymers of any of the foregoing are non-limiting examples of biocompatible polymers useful for manufacturing the implantable drainage devices.

In one example, a thermoformable medical drainage device, biliary stent or catheter, may be modified to form one embodiment of the drainage stent 10. For example, the medical drainage device may comprise of Polyurethane and may have an external diameter 35 of 8.5 F and a total length of 40 cm (a similar biliary drainage catheter is sold under the registered trademark "ULTRATHANE" by Cook Incorporated, Bloomington, Ind.—ULT8.5-38-40-32S-BCL). The planar curvilinear bends 16 with a lateral distance 36 of 12 mm can be formed at one end portion of the drainage device 10 by applying heat to said portion and mechanically manipulating said portion. Planar curvilinear bends 16 can also be formed at other portions of the drainage device 10 using the same steps described above. The curvilinear bends may be formed by heating a polymeric tubular member 12 above a temperature to soften the polymer and permit reshaping or thermoforming of the tubular member 12, followed by cooling to a temperature sufficient to retain the bent configuration. Furthermore, using the same steps described above, a variety of configurations of bends, varying number and size of bends, and different depths and pitches can be formed to accommodate different delivery devices and different anatomical features of the body vessel at the site of implantation. The planar curvilinear bends 16 of this embodiment may be more compliant and less voluminous than a pigtail loop, helical structure, or spiral design. Accordingly, this embodiment may be less traumatic and may cause less aggravating inflammation to the surrounding ductal tissue.

The implantable drainage devices, such as the drainage stent 10 or a drainage catheter, may be configured for percutaneous delivery, for example by sliding the drainage device over a guidewire. Preferably, each bend 23 in the tubular member 12 is flexible and resilient enough to permit the tubular member 12 to straighten upon elongation or application of lateral force to the bends to a coaxial (straight) configuration, and to resume a bent configuration when the tension or force on the bent portion is relaxed. In the coaxial configuration, the drainage stent 10 has a straight, tubular drainage lumen 18 without a tortuous portion, and is preferably symmetrically radially disposed around the longitudinal axis 19.

Figure 4:
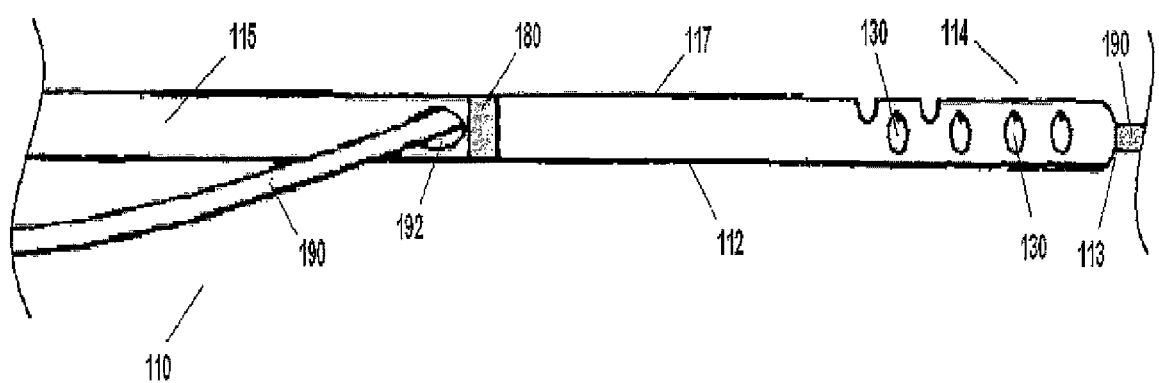
FIG. 4 is a side view of the drainage device shown in FIG. 2A on a guidewire.

The distal portion 14 of a tubular member 12 is preferably resiliently moveable from the bent configuration (illustrated in FIG. 2A) to a substantially linear configuration without the bends (illustrated in FIG. 4) when the tubular member 12 is longitudinally stretched under a suitable tension. The bent configuration can include the two or more planar curvilinear bends 16, as shown in FIGS. 2A-3B above. Desirably, the distal portion 14 is formed of a resilient material permitting the tubular member 12 to spontaneously assume the bent configuration absent longitudinal tension or lateral compression. FIG. 4 shows the distal portion 114 of a drainage stent 110 similar to the drainage stent 10 depicted in FIGS. 2A-3 in a linear configuration. The drainage stent 110 may be formed from a resiliently flexible tubular member 112 longitudinally stretched to maintain one or more curvilinear bends in a substantially linear configuration and mounting the straightened drainage stent on a guidewire 190 passing through the outlet 113, through the drainage lumen of the distal portion 114, through the central portion 117 and out of the drainage lumen through an access port 192 in the wall of the central portion 117 of the tubular member 112. The tubular member 112 may extend to the proximal portion 115, terminating in an inlet (not shown). The drainage stent 110 includes a plurality of holes 130 configured to maintain drainage of fluid from the inlet to the outlet 113 within a body vessel.

A drainage device, such as the drainage stent 110, may also include a means for orienting or viewing the orientation or position of the medical drainage device within a body vessel. For example, an endolumenal medical drainage device or a medical drainage device delivery system can comprise radiopaque indicia providing information on the position or the orientation of the medical drainage device within a body vessel. An endolumenal medical drainage device or delivery device may comprise one or more radiopaque materials to facilitate tracking and positioning of the medical drainage device. In FIG. 4, the outside of the tubular member 112 includes a radiopaque marker 180 configured for detection within the body by any suitable imaging technique. The radiopaque marker 180 may comprise one or more radiopaque materials applied by any fabrication method or absorbed into or sprayed onto the surface of part or all of the medical drainage device to form one or more marker bands. A marker band may be formed from a suitably radiopaque material. Radiopacity may be imparted to the marker band by covalently binding iodine to the polymer monomeric building blocks of the elements of the medical drainage device. Common radiopaque materials include barium sulfate, bismuth subcarbonate, and zirconium dioxide. Other radiopaque elements include: cadmium, tungsten, gold, tantalum, bismuth, platinum, iridium, and rhodium. In one preferred embodiment, iodine may be employed for its radiopacity and antimicrobial properties. Radiopacity is typically determined by fluoroscope or x-ray film. Imagable markers, formed from radiopaque material, can be incorporated in any portion of a medical drainage device. For example, radiopaque markers can be used to identify a long axis or a short axis of a drainage tube within a body vessel. A radiopaque material may be attached to a drainage tube of a drainage stent 110. The marker band can provide a means for orienting endolumenal medical drainage device within a body lumen. The marker band can be identified by remote imaging methods including X-ray, ultrasound, Magnetic Resonance Imaging and the like, or by detecting a signal from or corresponding to the marker. For example, marker bands may be provided at one or both of the inlet and outlet of a biliary drainage stent 110. The delivery system may also include radiopaque indicia. Examples of delivery systems including such indicia include the delivery systems described in US 2005/007082 A1, filed Jul. 29, 2004 by Deal et al., incorporated herein by reference in its entirety, which may be used to deliver a drainage device according to the first embodiment into a body vessel.

In a second embodiment, methods of delivering the medical devices of the first embodiment are provided. Referring to FIG. 5A, the drainage stent 110 can be delivered to a point of treatment 200 within a body vessel in any suitable manner. Preferably, the endolumenal medical drainage device is delivered percutaneously. For example, a biliary stent can be inserted into a biliary lumen in one of several ways: by inserting a needle through the abdominal wall and through the liver (a percutaneous transhepatic cholangiogram or "PTC"), by cannulating the bile duct through an endoscope inserted through the mouth, stomach, and duodenum (an endoscopic retrograde cholangiogram or "ERCP"), or by direct incision during a surgical procedure. A preinsertion examination, PTC, ERCP, or direct visualization at the time of surgery may be performed to determine the appropriate position for stent insertion. A guidewire may then be advanced through a lesion and a delivery catheter may be passed over the guidewire to allow the stent to be inserted.

In general, plastic stents are placed using a pusher tube over a guidewire with or without a guiding catheter. A drainage device delivery system may include the drainage device described above, disposed in the linear configuration around a guidewire positioned within the drainage lumen of the drainage device. The curvilinear portion of the tubular member may form a bent configuration within the delivery system when the guidewire is removed from the drainage lumen of the drainage device. The delivery system may further comprise at least one of a guiding catheter or a pusher catheter adapted to slideably receive the guidewire. Delivery systems are now available for plastic stents that combine the guiding and pusher catheters (such as one sold under the registered trademark "OASIS" by Cook Endoscopy, Winston-Salem, N.C.). The stent may be placed in the biliary duct either by the conventional pushing technique or by mounting it on a rotatable delivery catheter having a stent engaging member engageable with one end of the stent. Typically, when the diagnostic exam is a PTC, a guidewire and delivery catheter may be inserted via the abdominal wall. If the original exam was an ERCP, the stent may be placed via the mouth. The stent may then positioned under radiologic, endoscopic, or direct visual control at a point of treatment 200, such as across the narrowing in the bile duct. The stent may be released using the conventional pushing technique. The delivery catheter may then be removed, leaving the stent to hold the bile duct open. A further cholangiogram may be performed to confirm that the stent is appropriately positioned. Alternatively, other endolumenal medical drainage devices can also be delivered to any suitable body vessel, such as a vein, artery, urethra, ureteral passage or portion of the alimentary canal.

Figure 5B:
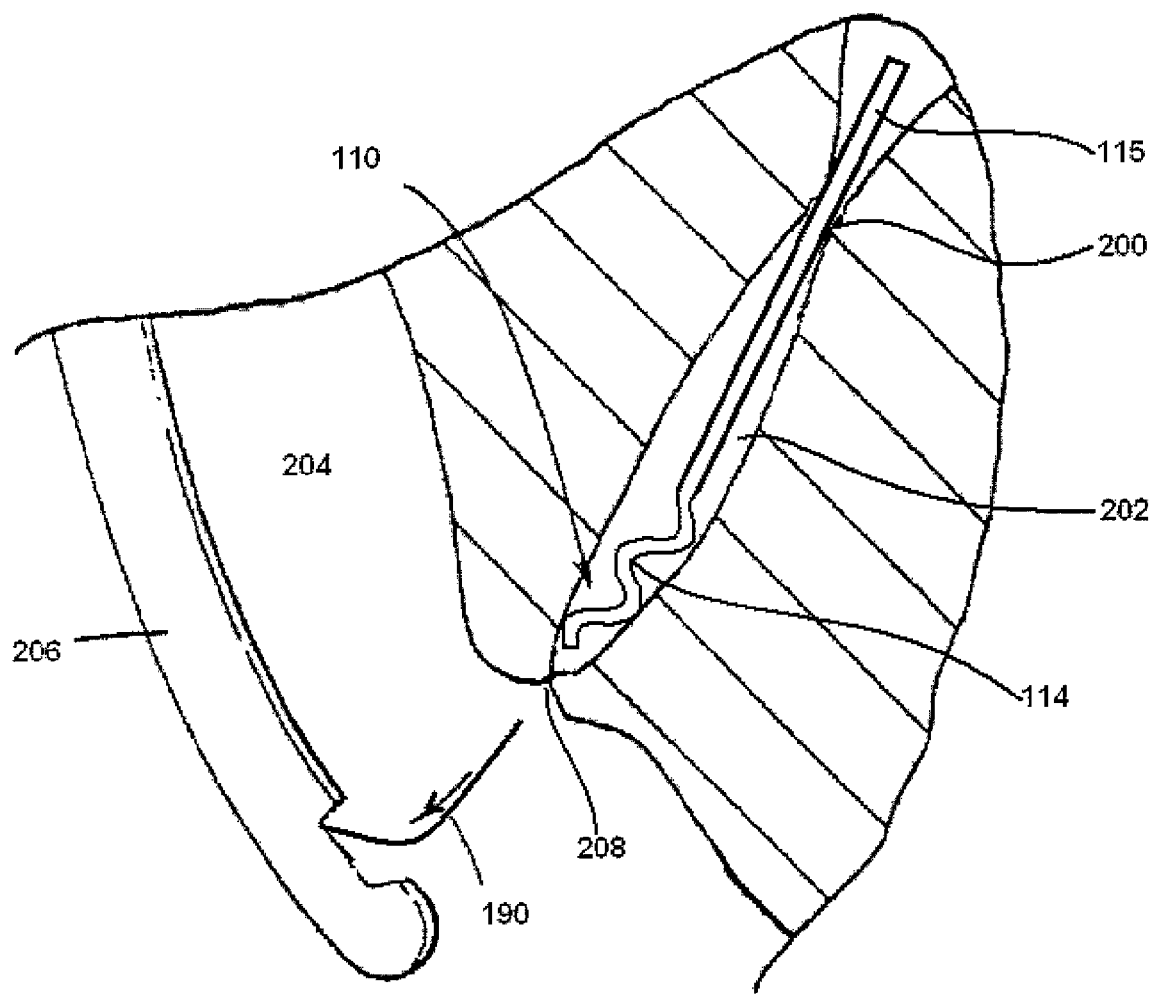
FIG. 5B shows placement of the drainage device into the biliary duct shown in FIG. 5B.

For example, drainage stent 110 may be advanced along the guidewire 190, preferably by a pushing action from a positioner located around the guidewire 190. FIGS. 5A-5B show an exemplary method of delivering the drainage stent 110 to a biliary duct, e.g., the common bile duct 202, using ERCP to the point of treatment 200. The drainage stent 110 and guidewire 190 assembly shown in FIG. 4 may be introduced to the duodenum 204 by any standard endoscopic technique for accessing the common bile duct 202, such as using a duodenoscope 206. The duodenoscope 206 may be introduced via the oral cavity into the duodenum 204 to visualize the Papilla of Vater 208 and Sphincter of Oddi, which lie at the opening to the common bile duct 202 and the pancreatic duct. In one exemplary method, the drainage stent 110 and guidewire 190 may be advanced from the accessory channel of the duodenoscope 206 to cannulate a portion of the common bile duct 202. As shown in FIG. 5A, the guidewire 190 may be advanced to the point of treatment 200 within the common bile duct 202, and the drainage stent 110 may be advanced over the guidewire 190.

For applications where the size of the scope channel is restricted or other applications where there is limited room to accommodate both devices side by side, the drainage stent 110 can be modified to allow for the guidewire to lie alongside without increasing the overall diameter. This can be done by forming an open channel (preferably one that would not capture the wire) or creating a flattened longitudinal portion along the length of the drainage stent 110. The position of the drainage stent 110 may be monitored by detecting a radiopaque portion 180 of the tubular member 112 using standard imaging techniques. After placement of the drainage stent 110 within the common bile duct 202, as shown in FIG. 5B, the guidewire 190 may be retracted into the duodenoscope 206. This permits the distal portion 114 of the tubular member 112 to resume a bent configuration comprising one or more planar dual-curve configurations. The curved distal portion 114 may be adapted to retain the tubular member 112 within the common bile duct 202, and may prevent migration of the tubular member 112 into the duodenum 204. The proximal portion 115 may be adapted to fit securably within the occluded biliary duct.

Figure 5C:
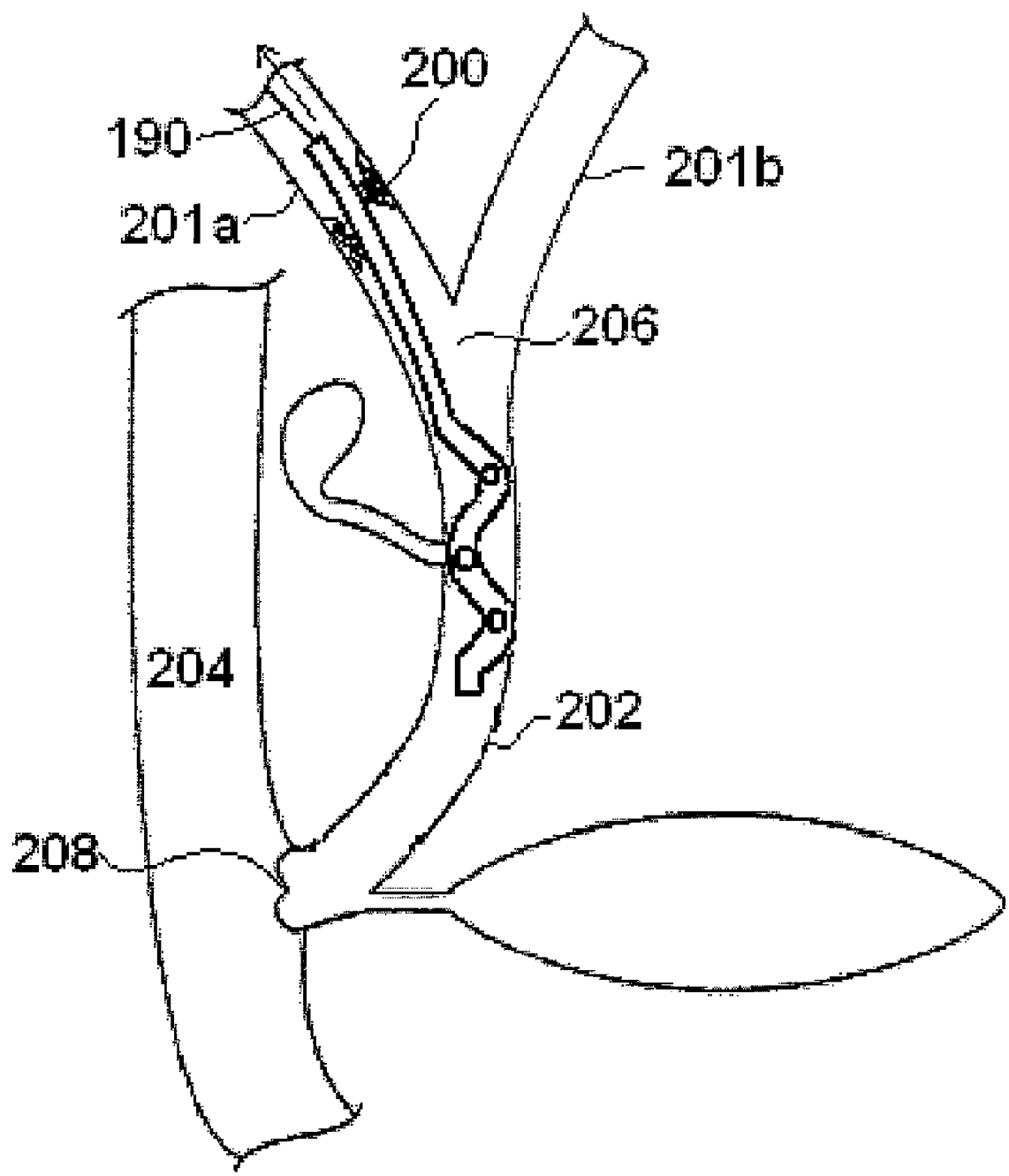
FIG. 5C shows placement of the drainage device into the biliary duct.

Preferably, however, the drainage device 110 is implanted percutaneously, without passing through the Sphincter of Oddi, without performing a sphincterotomy. This may reduce the likelihood of duodenobiliary reflux, which may lead to bacterial infection within the Papilla of Vater. Such infections may facilitate blockage of biliary stents due to bacterial deposition. FIG. 5C shows a preferred method of delivering the drainage stent 110 to a binary duct, e.g., the right hepatic duct 201a, using PTC. After a PTC is performed using conventional techniques, the guidewire 190 may be inserted and moved through the PTC catheter from the liver through the right hepatic duct 201a and the common hepatic duct 206 and may be placed through the point of treatment 200 within the biliary duct. Next, the PTC catheter may be removed leaving the guidewire 190 within the biliary duct. Using a delivery catheter, the drainage stent 110 may be advanced over the guidewire 190 and may be placed at the point of treatment 200 within the right hepatic duct 201a. More specifically, the distal portion 114 of the drainage stent 110 may be placed within the common bile duct 202, but not placed within or penetrated through the Sphincter of Oddi and Papilla of Vater 208 into the duodenum 204. After placement of the drainage stent 110 at the point of treatment 200 within the right hepatic duct 201a and the common bile duct 202, the delivery catheter and, as shown in FIG. 5C, the guidewire 190 is retracted, permitting the distal portion 114 of the tubular member 112 to resume a bent configuration comprising one or more planar dual-curve configurations. The drainage stent 110 is retained within the biliary duct, without transversing the Sphincter of Oddi, and without being positioned within the duodenum 204. The curved distal portion 114 is adapted to retain the tubular member 112 within the biliary duct, and prevent migration of the tubular member 112 into the duodenum 204. The proximal portion 115 may be adapted to fit securably within the occluded biliary duct. With the position of the drainage device not extending through the Sphincter of Oddi and Papilla of Vater into the duodenum and with this method of implantation, compromising the Sphincter of Oddi and its function may be avoided, which may also reduce the risk of duodenobiliary reflux.

The invention includes other embodiments within the scope of the claims, and variations of all embodiments, and is limited only by the claims made by the Applicants. Additional understanding of the invention can be obtained by referencing the detailed description of embodiments of the invention, below, and the appended drawings.

We claim:

1. A method of deploying a drainage device within the Papilla of Vater, where the drainage device is a biliary stent comprising a tubular member having proximal and distal ends, interior and exterior surfaces, a tubular member thickness between the interior and exterior surfaces, and a drainage lumen disposed within the interior surface between the proximal end and the distal end, the method comprising:

inserting a wire guide into a body vessel and advancing a distal end of the wire guide to a point of treatment within the Papilla of Vater;

inserting the drainage device into a body vessel in a linear configuration, the drainage device having a curvilinear portion of the tubular member resiliently moveable between the linear configuration and a bent configuration, the bent configuration comprising a pair of adjacent curvilinear bends in the tubular member bent in opposite directions with respect to one another and radially bisected by a hypothetical plane containing the longitudinal axis, the linear configuration being formed by extending the curvilinear portion of the drainage device along the longitudinal axis until the longitudinal axis is contained within the drainage lumen between the proximal end and the distal end, the curvilinear portion being extended along the longitudinal axis by disposing the wire guide through the drainage lumen of at least the curvilinear portion, the drainage device further comprising a substantially linear portion positioned proximal to the curvilinear portion when in the bent configuration;

delivering the drainage device in the linear configuration to the point of treatment within the Papilla of Vater by advancing the drainage device along the wire guide; and deploying the drainage device at the point of treatment in the bent configuration with the pair of curvilinear bends securing the drainage device within the body vessel and permitting fluid to flow through the drainage lumen, where the drainage device is oriented so that bodily fluid passing through the drainage device enters the drainage lumen through the linear portion and exits the drainage lumen through the curvilinear portion.

2. The method of claim 1, where the point of treatment is a biliary duct.

3. The method of claim 2, where the drainage device does not transverse the Sphincter of Oddi when deployed at the point of treatment.

4. The method of claim 1, where the drainage device is delivered without performing a sphincterotomy at the Sphincter of Oddi.

5. The method of claim 2, where the curvilinear portion is positioned within the biliary duct at the point of treatment closer to the Sphincter of Oddi than the linear portion.

6. The method of claim 1, where the tubular member thickness is uniform along the entire length of the tubular member from the proximal end to the distal end.

7. The method of claim 1, where the tubular member is free of a helical or loop bend.

8. The method of claim 1, where each pair of consecutive bends forms an "S- shaped" configuration in the plurality of curvilinear bends having a ratio between the longitudinal length and lateral width of each pair of consecutive bends in the tubular member of between about 1.0:1.0 and about 1.0:20.0.

9. The method of claim 8, where the ratio is between about 1.0:1.6 and 1.0:2.4.

10. The method of claim 1, where the longitudinal length of each individual curvilinear bend measured along the longitudinal axis is about 42%-100% of the width of the curvilinear bend measured perpendicular to the longitudinal axis.

11. The method of claim 1, where the tubular member is formed from a thermoformable polymer.

12. The method of claim 1, where the tubular member thickness is substantially uniform along entire length of the tubular member from the proximal end to the distal end; and where the internal radius (r) of a pair of two adjacent curvilinear bends is characterized by the relationship: $r=(w/2)-d$, where w is the width of the pair of adjacent curvilinear bends measured perpendicular to the longitudinal axis of the tubular member in the linear configuration and d is an external diameter of the tubular member.

13. The method of claim 1, wherein the curvilinear portion of the tubular member has a longitudinal length of about 10-25 mm.

14. The method of claim 1, wherein the curvilinear portion has a lateral distance of about 8-12 mm, the lateral distance being measured perpendicular to the longitudinal axis between vertices of the adjacent curvilinear bends.

15. The method of claim 1, wherein the adjacent curvilinear bends of the curvilinear portion have a longitudinal length measured parallel to the longitudinal axis between the vertices of the adjacent curvilinear bends is about 40%-100% of the lateral distance measured perpendicular to the longitudinal axis between the vertices of the adjacent curvilinear bends.

16. The method of claim 1, where an access port is disposed in the linear portion at and intermediate location between the proximal and distal ends of the drainage device, the access port extending between the interior and exterior surfaces and in communication with the drainage lumen, and further where the wire guide extends through the access port as the drainage device is advanced along the wire guide.

17. The method of claim 1, where the proximal end and the distal end of the drainage device both intersect the longitudinal axis when in the bent configuration.

* * * * *